(12) United States Patent
Oliverius et al.

(10) Patent No.: US 10,507,317 B2
(45) Date of Patent: Dec. 17, 2019

(54) CONNECTOR SHIELD FOR SENSOR ENABLED MEDICAL DEVICES

(71) Applicant: St. Jude Medical International Holding S.à r.l., Luxembourg (LU)

(72) Inventors: Andrew Oliverius, Eagan, MN (US); James Marrs, Arden Hills, MN (US); Varun Bansal, Plymouth, MN (US); Timothy S. Marass, Minneapolis, MN (US)

(73) Assignee: ST JUDE MEDICAL INTERNATIONAL HOLDING S.À R.L., Luxembourg (LU)

( * ) Notice: Subject to any disclaimer, the term of this patent is extended or adjusted under 35 U.S.C. 154(b) by 27 days.

(21) Appl. No.: 15/392,812

(22) Filed: Dec. 28, 2016

(65) Prior Publication Data

US 2017/0189664 A1    Jul. 6, 2017

Related U.S. Application Data

(60) Provisional application No. 62/273,885, filed on Dec. 31, 2015.

(51) Int. Cl.
*A61M 39/10* (2006.01)
*A61B 5/00* (2006.01)
(Continued)

(52) U.S. Cl.
CPC ............. *A61M 39/10* (2013.01); *A61B 5/062* (2013.01); *A61B 5/6852* (2013.01); *A61B 18/1492* (2013.01); *A61B 34/20* (2016.02); *A61M 25/0068* (2013.01); *A61M 25/0136* (2013.01); *A61M 25/0147* (2013.01); *A61B 5/0044* (2013.01); *A61B 2017/00022* (2013.01); *A61B 2017/00292* (2013.01);
(Continued)

(58) Field of Classification Search
CPC .......... A61B 2562/18; A61B 2562/182; A61B 18/1492; A61B 34/20; A61B 5/062; A61B 5/6852; A61B 2034/2051; A61B 2017/00292; A61B 2018/00178; A61B 5/0044; A61M 39/10; A61M 25/0068; A61M 25/0136; A61M 25/0147; A61M 2025/0166
See application file for complete search history.

(56) References Cited

U.S. PATENT DOCUMENTS 6,233,476 B1    5/2001    Strommer et al.
6,498,944 B1    12/2002    Ben-Haim et al.
(Continued)

FOREIGN PATENT DOCUMENTS

EP    1731917 A2    12/2006
JP    2015518411 A    7/2015
WO    2013166397 A1    11/2013

*Primary Examiner* — Kaylee R Wilson
(74) *Attorney, Agent, or Firm* — Dykema Gossett PLLC

(57) ABSTRACT

Various embodiments of the present disclosure can include a medical device assembly. The medical device assembly can comprise an elongate hollow cylindrical body that extends along a longitudinal axis. A distal cap portion can extend along the longitudinal axis. A proximal end of the distal cap portion can be connected to a distal end of the elongate hollow cylindrical body. A wire management port can be defined in the distal cap portion.

18 Claims, 12 Drawing Sheets

(51) Int. Cl.
*A61B 5/06* (2006.01)
*A61B 34/20* (2016.01)
*A61M 25/00* (2006.01)
*A61M 25/01* (2006.01)
*A61B 18/14* (2006.01)
*A61B 17/00* (2006.01)
*A61B 18/00* (2006.01)

(52) U.S. Cl.
CPC ............... *A61B 2017/00477* (2013.01); *A61B 2018/00178* (2013.01); *A61B 2034/2051* (2016.02); *A61B 2562/18* (2013.01); *A61M 2025/0166* (2013.01); *A61M 2205/02* (2013.01)

(56) References Cited

U.S. PATENT DOCUMENTS

| | | |
|---|---|---|
| 6,690,963 B2 | 2/2004 | Ben-Haim et al. |
| 6,788,967 B2 | 9/2004 | Ben-Haim et al. |
| 7,197,354 B2 | 3/2007 | Sobe |
| 7,386,339 B2 | 6/2008 | Strommer et al. |
| 2007/0212926 A1 | 9/2007 | Nakaura et al. |
| 2008/0306380 A1 | 12/2008 | Parchak et al. |
| 2012/0071752 A1 | 3/2012 | Sewell et al. |
| 2014/0039302 A1 | 2/2014 | Miller et al. |
| 2015/0094654 A1 | 4/2015 | Bansal et al. |
| 2016/0227325 A1* | 8/2016 | Pare ......................... H04R 1/06 |

* cited by examiner

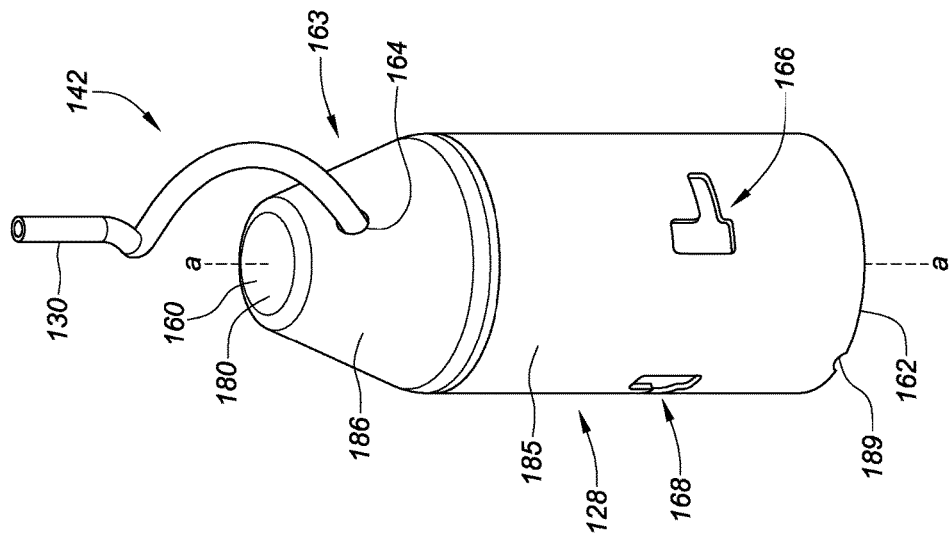
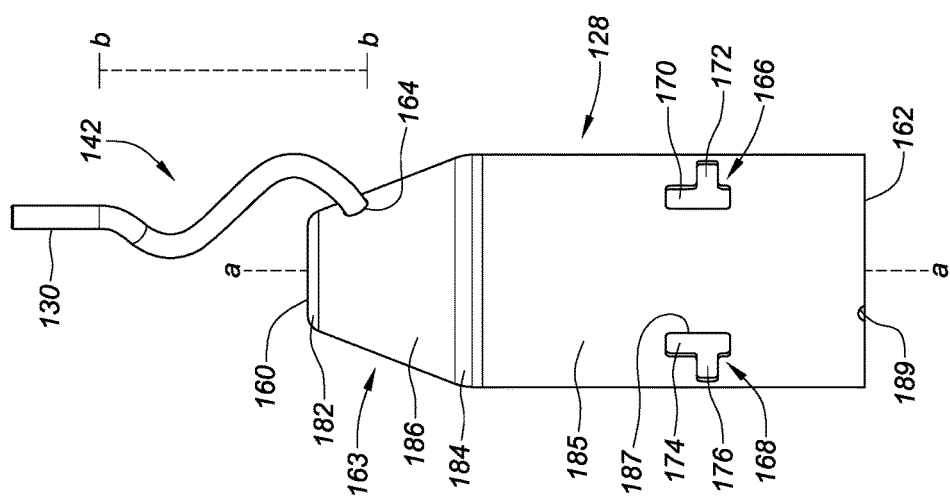

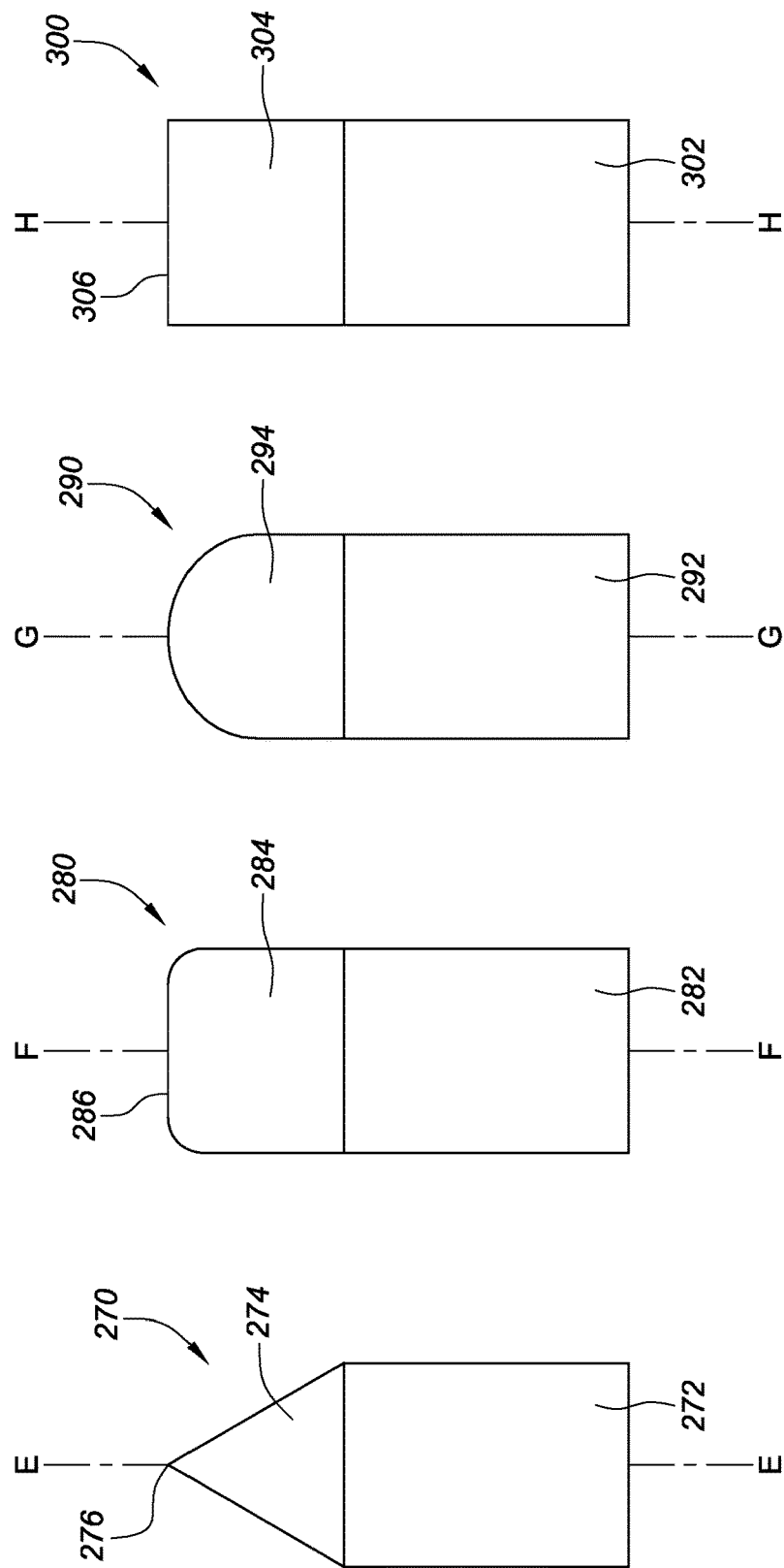

CONNECTOR SHIELD FOR SENSOR ENABLED MEDICAL DEVICES

CROSS-REFERENCE TO RELATED APPLICATION

This application claims priority to U.S. provisional patent application No. 62/273,885 entitled "CONNECTOR SHIELD FOR SENSOR ENABLED DEVICES", filed 31 Dec. 2015, which is hereby incorporated by reference as though fully set forth herein.

BACKGROUND a. Field

This disclosure relates to a connector shield for sensor enabled medical devices.

b. Background

A number of different types of medical positioning systems may be used to aid in the performance of various medical diagnostic and/or therapeutic procedures relating to different parts of the human anatomy, such as, for example, the heart. Among other things, and generally speaking, these systems may provide the ability to determine the position and/or position and orientation (P&O) of one or more sensor enabled medical devices disposed within the body of the patient, such as, for example, catheters and sheaths, for visualization and navigation purposes.

One such type of medical positioning system is a magnetic field-based medical positioning system. Magnetic field-based positioning systems can include one or more magnetic field generators connected to or placed near the patient bed or another component in the operating environment (e.g., a distal end of a sensor enabled medical device). The field generators can be configured to provide controlled, low-strength AC magnetic fields in an area of interest (i.e., an anatomical region) and can be used to determine and track one or more magnetic sensors disposed in or on a sensor enabled medical device disposed within the area of interest. More particularly, each magnetic sensor, which may comprise a magnetic coil, can be configured to detect and generate a respective signal indicative of one or more characteristics of the magnetic field(s). The medical positioning system then processes the generated signals to produce one or more P&O readings associated with the sensors (and thus the sensor enabled medical device). The P&O of the sensor enabled medical device can thereafter be tracked relative to the magnetic field(s).

As briefly described above, medical devices that may be used with such medical positioning systems include elongate medical devices such as catheters and sheaths. These medical devices generally comprise an elongate shaft having a proximal end portion, a distal end portion, and one or more sensors mounted in or on the shaft at or near the distal end portion thereof. As also briefly described above, the sensors of the sensor enabled medical device may comprise magnetic sensors in the form of coils and/or electrodes that are configured to allow the system to determine the position and/or P&O of the sensor, and therefore by extension, the sensor enabled medical device.

BRIEF SUMMARY

Various embodiments of the present disclosure can include a medical device assembly. The medical device assembly can comprise an elongate hollow cylindrical body that extends along a longitudinal axis. A distal cap portion can extend along the longitudinal axis. A proximal end of the distal cap portion can be connected to a distal end of the elongate hollow cylindrical body. A wire management port can be defined in the distal cap portion.

Various embodiments of the present disclosure can include a medical device assembly. The medical device assembly can comprise an elongate hollow cylindrical body that extends along a longitudinal axis. An elongate hollow distal portion can extend along the longitudinal axis. A proximal end of the elongate hollow distal portion can be connected to a distal end of the elongate hollow cylindrical body. The elongate hollow distal portion can be frustoconical in shape, and the elongate hollow distal portion can define a wire management port that extends through a sidewall of the elongate hollow distal portion. A distal face can be connected to a distal end of the elongate hollow distal portion.

Various embodiments of the present disclosure can include a medical device assembly. The medical device assembly can comprise a connector shield formed from a magnetically permeable material. The connector shield can include an elongate hollow cylindrical body that extends along a longitudinal axis. The connector shield can include an elongate hollow distal portion that extends along the longitudinal axis. A proximal end of the elongate hollow distal portion can be connected to a distal end of the elongate hollow cylindrical body. The elongate hollow distal portion can be frustoconical in shape and the elongate hollow distal portion can define a wire management port extending through a sidewall of the elongate hollow distal portion. A distal face can be connected to a distal end of the elongate hollow distal portion. The cylindrical body, distal portion, and distal face can be formed from a magnetically permeable material. An electromechanical connector can be disposed in a lumen defined by the connector shield. A twisted pair of wires can be connected to a distal end of the electromechanical connector, the twisted pair of wires extending distally through the wire management port.

BRIEF DESCRIPTION OF THE DRAWINGS

FIG. 5A is a side view of a connector shield and a wire management tube, as depicted in FIG. 4, in accordance with embodiments of the present disclosure.

FIG. 5B is an isometric side and distal view of the connector shield and the wire management tube depicted in FIG. 5A, in accordance with embodiments of the present disclosure.

FIGS. 7A to 7D are side views of connector shields with various profiles, in accordance with embodiments of the present disclosure.

DETAILED DESCRIPTION

Figure 1:
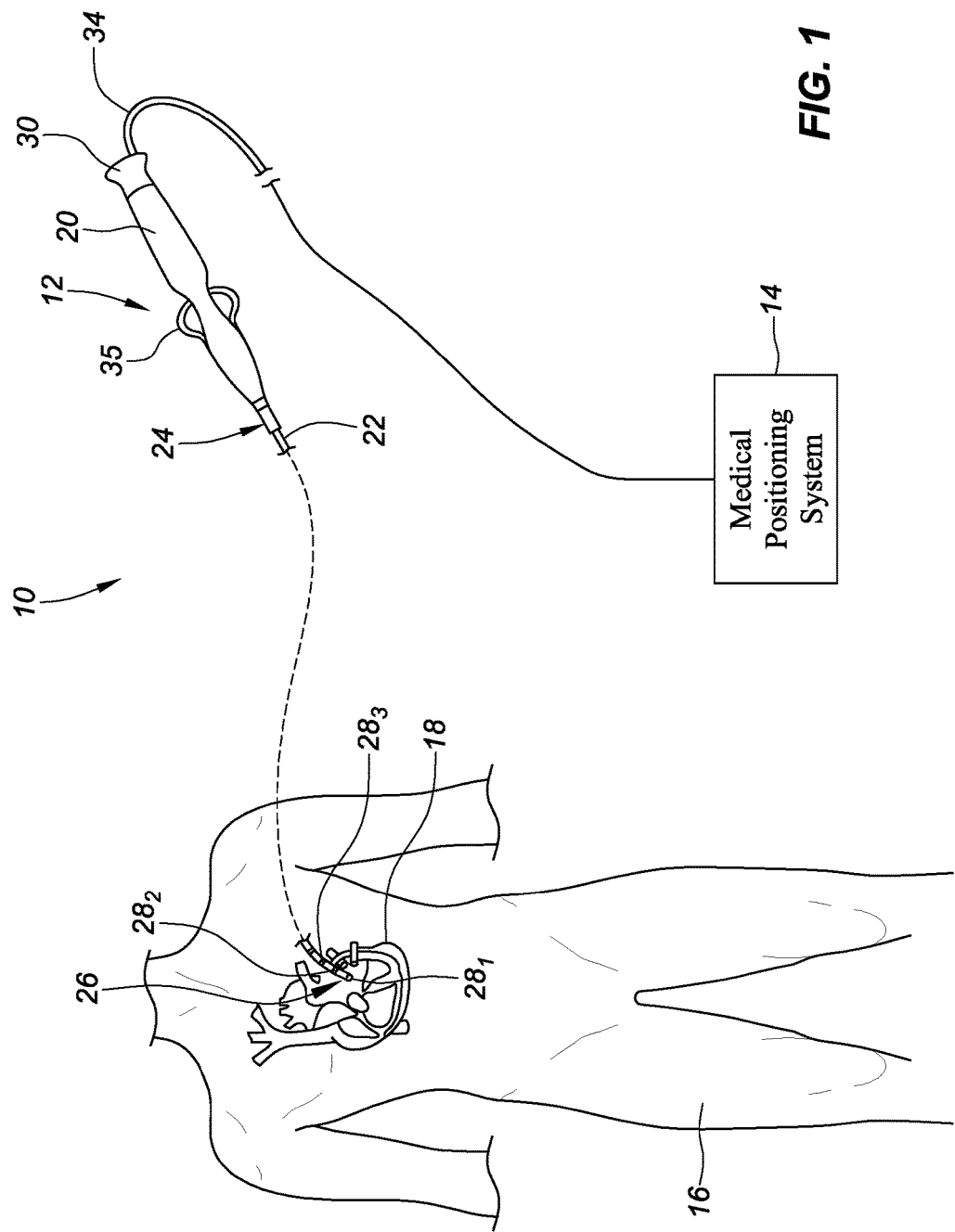
FIG. 1 is a diagrammatic view of a system for performing one or more diagnostic or therapeutic procedures, wherein the system comprises a magnetic field-based medical positioning system, in accordance with embodiments of the present disclosure.

Referring now to the drawings wherein like reference numerals are used to identify identical or similar components in the various views, FIG. 1 illustrates one embodiment of a system 10 for performing one or more diagnostic and/or therapeutic medical procedures relating to different parts of the human anatomy, such as, for example, the heart. For purposes of clarity and illustration, the description set forth below will be with respect to a system used for cardiac-related applications only. It should be understood, however, that the present disclosure may be implemented and find use in connection with any number of other anatomical-related applications. Accordingly, the present disclosure is not intended to be limited to cardiac-related applications.

FIG. 1 is a diagrammatic view of a system 10 for performing one or more diagnostic or therapeutic procedures, wherein the system comprises a magnetic field-based medical positioning system 14, in accordance with embodiments of the present disclosure. In some embodiments, and with reference to FIG. 1, the system 10 comprises a sensor enabled medical device 12 and a medical positioning system 14. The sensor enabled medical device 12 may comprise an elongate medical device such as, for example, a catheter or a sheath. For purposes of illustration and clarity, the description below will be limited to an embodiment wherein the sensor enabled medical device 12 comprises a catheter (catheter 12). It will be appreciated, however, that the present disclosure is not meant to be limited to such an embodiment, but rather in other embodiments, the sensor enabled medical device 12 may comprise other elongate medical devices, such as, for example and without limitation, sheaths, introducers and the like.

With continued reference to FIG. 1, the catheter 12 is configured to be inserted into a patient's body 16, and more particularly, into the patient's heart 18. The catheter 12 may include a catheter actuator 20 (e.g., catheter handle), a shaft 22 having a proximal end portion 24 and a distal end portion 26, and one or more sensors 28 mounted in or on the shaft 22 of the catheter 12. As used herein, "sensor 28" or "sensors 28" may refer to one or more sensors $28_1$, $28_2$, ... $28_N$, as appropriate and as generally illustrated. In one embodiment, the sensors 28 are disposed at the distal end portion 26 of the shaft 22. The catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads. In one embodiment, the catheter 12 further comprises an electromechanical connector 30 configured to allow the catheter 12, and the sensors 28 thereof, in particular, to be coupled with other components of the system 10, such as, for example, the medical positioning system 14.

The catheter actuator 20, which is disposed at the proximal end portion 24 of the shaft 22, provides a location for the clinician to hold the catheter 12 and may further provide means for steering or guiding the shaft 22 within the body 16 of a patient. As depicted, the catheter actuator 20 can be bi-directional and can include one or more actuators (e.g., actuator 35), which can be selectively manipulated to cause the shaft 12 to deflect in one or more directions (e.g., up, down or left, right). For example, the catheter actuator 20 may include means to manipulate one or more steering wires extending through the catheter 12 to the distal end portion 26 of the shaft 22 to steer the shaft 22. The catheter actuator 20 is conventional in the art and it will be understood that the construction of the catheter actuator 20 may vary. Although a bi-directional catheter actuator 20 is depicted in FIG. 1, any type of catheter actuator can be used with embodiments of the present disclosure, for example, those depicted in relation to FIGS. 2A and 2B. In another embodiment, the catheter 12 may be robotically driven or controlled. Accordingly, in such an embodiment, rather than a clinician manipulating a catheter actuator to steer or guide the catheter 12, and the shaft 22 thereof, in particular, a robot is used to manipulate the catheter 12.

Figure 2A:
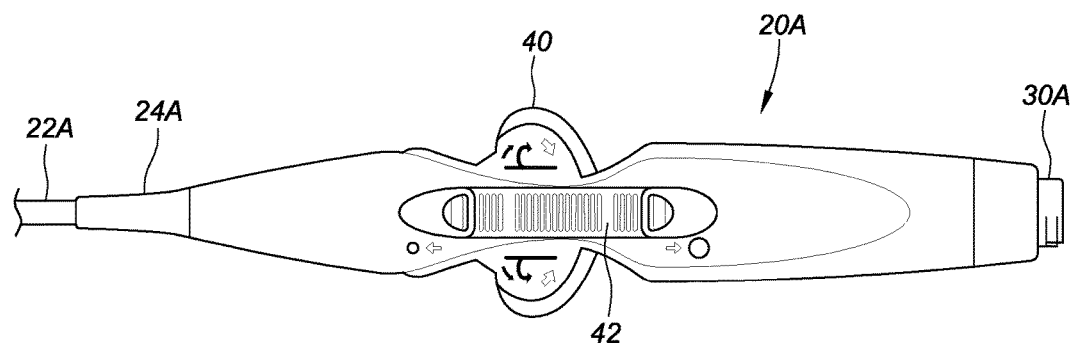
FIG. 2A is a diagrammatic view of a bi-directional catheter actuator of a sensor enabled medical device, configured for use in the system illustrated in FIG. 1, in accordance with embodiments of the present disclosure.

FIG. 2A is a diagrammatic view of a bi-directional catheter actuator 20A of a sensor enabled medical device, configured for use in the system 10 illustrated in FIG. 1, in accordance with embodiments of the present disclosure. The catheter actuator 20A, which is disposed at the proximal end portion 24A of the shaft 22A, provides a location for the clinician to hold the catheter and may further provide means for steering or guiding the shaft 22A within the body of a patient. As depicted, the catheter actuator 20A can be omni-directional and can include one or more actuators (e.g., actuators 40, 42), which can be selectively manipulated to cause the shaft 22A to deflect in one or more directions (e.g., up, down, left, and/or right). For example, the catheter actuator 20A may include means to manipulate one or more steering wires extending through the catheter to a distal end portion of the shaft 22A to steer the shaft 22A. The catheter actuator 20A is conventional in the art and it will be understood that the construction of the catheter actuator 20A may vary.

Figure 2B:
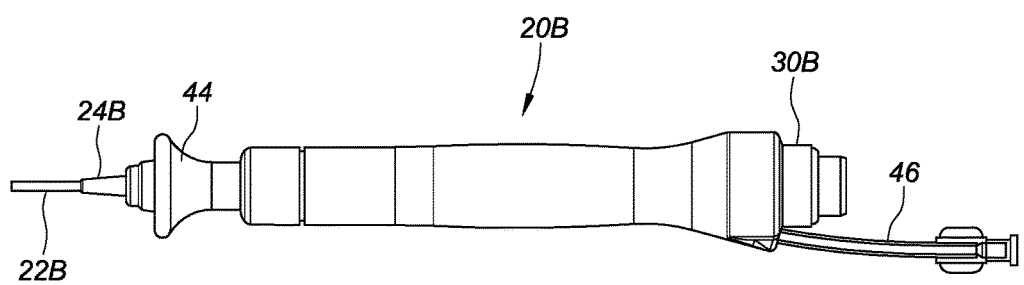
FIG. 2B is a diagrammatic view of a uni-directional catheter actuator of a sensor enabled medical device, configured for use in the system illustrated in FIG. 1, in accordance with embodiments of the present disclosure.

FIG. 2B is a diagrammatic view of a uni-directional catheter actuator 20B of a sensor enabled medical device, configured for use in the system 10 illustrated in FIG. 1, in accordance with embodiments of the present disclosure. The catheter actuator 20B, which is disposed at the proximal end portion 24B of the shaft 22B, provides a location for the clinician to hold the catheter and may further provide means for steering or guiding the shaft 22B within the body of a patient. As depicted, the catheter actuator 20B can be uni-directional and can include an actuator (e.g., plunger assembly 44), which can be selectively manipulated to cause the shaft 22B to deflect in a single direction (e.g., up, down, left, or right). For example, the catheter actuator 20B may include means to manipulate one or more steering wires extending through the catheter to a distal end portion of the shaft 22B to steer the shaft 22B. In some embodiments, the catheter actuator 20B can include an irrigation tube 46, which can extend from a proximal end of the catheter actuator 20B. The irrigation tube 46 can be used to provide fluid to a distal portion of the shaft 22B in relation to a diagnostic and/or therapeutic procedure. The catheter actuator 20B is conventional in the art and it will be understood that the construction of the catheter actuator 20B may vary.

With further reference to FIG. 1, the shaft 22 is an elongate, tubular, flexible member configured for movement within the body 16. The shaft 22 supports, for example and without limitation, magnetic sensors and/or electrodes mounted thereon, such as, for example, the sensors 28, associated conductors, and possibly additional electronics used for signal processing and conditioning. The shaft 22 may also permit transport, delivery, and/or removal of fluids (including irrigation fluids, cryogenic ablation fluids, and bodily fluids), medicines, and/or surgical tools or instruments. The shaft 22 may be made from conventional materials such as polyurethane, and defines one or more lumens configured to house and/or transport electrical conductors, fluids, or surgical tools. The shaft 22 may be introduced into a blood vessel or other structure within the body 16 through a conventional introducer. The shaft 22 may then be steered or guided through the body 16 to a desired location, such as the heart 18, using means well known in the art.

The sensors 28 mounted in or on the shaft 22 of the catheter 12 may be provided for a variety of diagnostic and therapeutic purposes including, for example and without limitation, electrophysiological studies, pacing, cardiac mapping, and ablation. In one embodiment, one or more of the sensors 28 are provided to perform a location or position sensing function. More particularly, and as will be described in greater detail below, one or more of the sensors 28 are configured to be a position sensor that provides information relating to the location (position and orientation, or "P&O") of the catheter 12, and the distal end portion 26 of the shaft 22 thereof, in particular, at certain points in time. Accordingly, in such an embodiment, as the catheter 12 is moved along a surface of a structure of interest of the heart 18 and/or about the interior of the structure, the sensor(s) 28 can be used to collect location data points that correspond to the surface of, and/or other locations within, the structure of interest. These location data points can then be used for a number of purposes such as, for example and without limitation, the construction of surface models of the structure of interest. For purposes of clarity and illustration, the description below will be with respect to an embodiment wherein a single sensor 28 of the catheter 12 comprises a position sensor. It will be appreciated, however, that in other embodiments, which remain within the spirit and scope of the present disclosure, the catheter 12 may comprise more than one position sensors, as well as other sensors or electrodes configured to perform other diagnostic and/or therapeutic functions.

In some embodiments, the electromechanical connector 30 can provide electrical and mechanical connection(s) for, among other things, leads of the sensor 28 of the catheter 12, as well as wires or cables, such as, for example, a cable 34 extending between the catheter 12 and other components of the system 10 (e.g., the medical positioning system 14, an ablation generator, an electrophysiology recording system, a junction box, a stimulation system, a tissue contact sensing system, etc.). In one embodiment, and as illustrated in FIG. 1, the electromechanical connector 30 can be disposed within the catheter actuator 20 of the catheter 12. In another embodiment, rather than being disposed within or as part of the catheter actuator 20, the electromechanical connector 30 can be disposed apart from the catheter actuator 20 (e.g., at the end of a pigtail extending from the catheter actuator 20 of the medical device 12).

Accordingly, regardless of the particular form the electromechanical connector 30 takes, it is configured to allow for the electrical connection of the catheter 12, and the sensor 28 thereof, to one or more components of the system 10, such as, for example, the medical positioning system 14.

One drawback to the use of these types of medical devices in conjunction with a magnetic field-based medical positioning system 14 is that any loops of wire that are considered separate or apart from the sensor can act as a magnetic pickup when subjected to magnetic fields. This may result in noise or interference being added to the signal generated by the sensor, thereby potentially adversely impacting the accuracy of the P&O determination based thereon (i.e., causing an error in the P&O of the sensor determined based on the signal generated by the sensor). For example, a wire that is wrapped numerous times around a core to form a coil may have two ends or leads extending from the coil. These leads are routed from the coil down the shaft 22 of the sensor enabled medical device 12 where they are terminated at an electromechanical connector 30 that allows for the sensor to be electrically coupled to other components of, for example, the medical positioning system 14 or components that are intermediate thereto (e.g., amplifiers, processors, etc.). However, when arranged within the shaft 22 of the sensor enabled medical device 12, these two leads may serve to form a loop of wire that may generate a current when subjected or exposed to a magnetic field. As described above, this may result in the addition of noise or interference to the current signal being transmitted from the sensor.

In the sensor enabled medical device 12 itself, one conventional technique used to address the above-described problem is to arrange the two leads of a sensor in a twisted pair pattern along the lengths of the leads from the sensor to the termination point. Such an arrangement is known to prevent, or at least substantially minimize, magnetic pickup in the leads. Accordingly, by preventing magnetic pickup along the length of the shaft 22 of the sensor enabled medical device 12, interference or noise that may adversely impact the signals generated and transmitted by the sensor is prevented or at least substantially minimized. However, while this technique has been useful in limiting interference generated along the length of the shaft 22 of the sensor enabled medical device 12, it does not completely solve the problem with respect to other areas or locations of the medical device or within the system of which it is a part.

As described above, the two leads of the sensor can be terminated at an electrical connector that can be disposed at or near the proximal end portion of the shaft 22 (e.g., within or near the catheter actuator of the device located proximate the proximal end portion of the shaft 22). A proximal portion of the twisted pair formed from the two leads of the sensor is untwisted at a proximal end of the twisted pair to allow each of the leads to be connected to a separate terminal. This untwisted portion of the twisted pair can form a loop, which can make the untwisted portion susceptible to interaction with the magnetic field generated by the medical positioning system 14, as discussed herein, causing signal noise to be generated. Thus, a majority of the length of the leads that connect the sensor to the electrical connector can be insusceptible or relatively insusceptible to the magnetic field causing noise to be generated in the leads. However, the untwisted portion of the twisted pair that is terminated at the electrical connector can be susceptible to the magnetic field, causing signal noise to be generated. Embodiments of the present disclosure can reduce a susceptibility of the untwisted portion to the magnetic field, thus preventing the generation of noise in a signal provided by the sensor. For example, as further discussed herein, embodiments of the present disclosure can include a connector shield that shields the untwisted portion of the twisted pair from the magnetic field.

Because the catheter actuator 20 of the medical device, and therefore, the electromechanical connector 30 to which the leads are coupled, are disposed in close proximity to the patient during a procedure, the electromechanical connector 30 and cable may be subjected or exposed to the magnetic field(s) applied by the medical positioning system 14. As a result, the electromechanical connector 30 can act as a magnetic pickup, and therefore, a current may be induced by the magnetic field(s). As described above, such a generated current may result in noise or interference to the signal generated and transmitted by the sensor, which may introduce not insignificant error in the sensor location determined therefrom.

Figure 3:
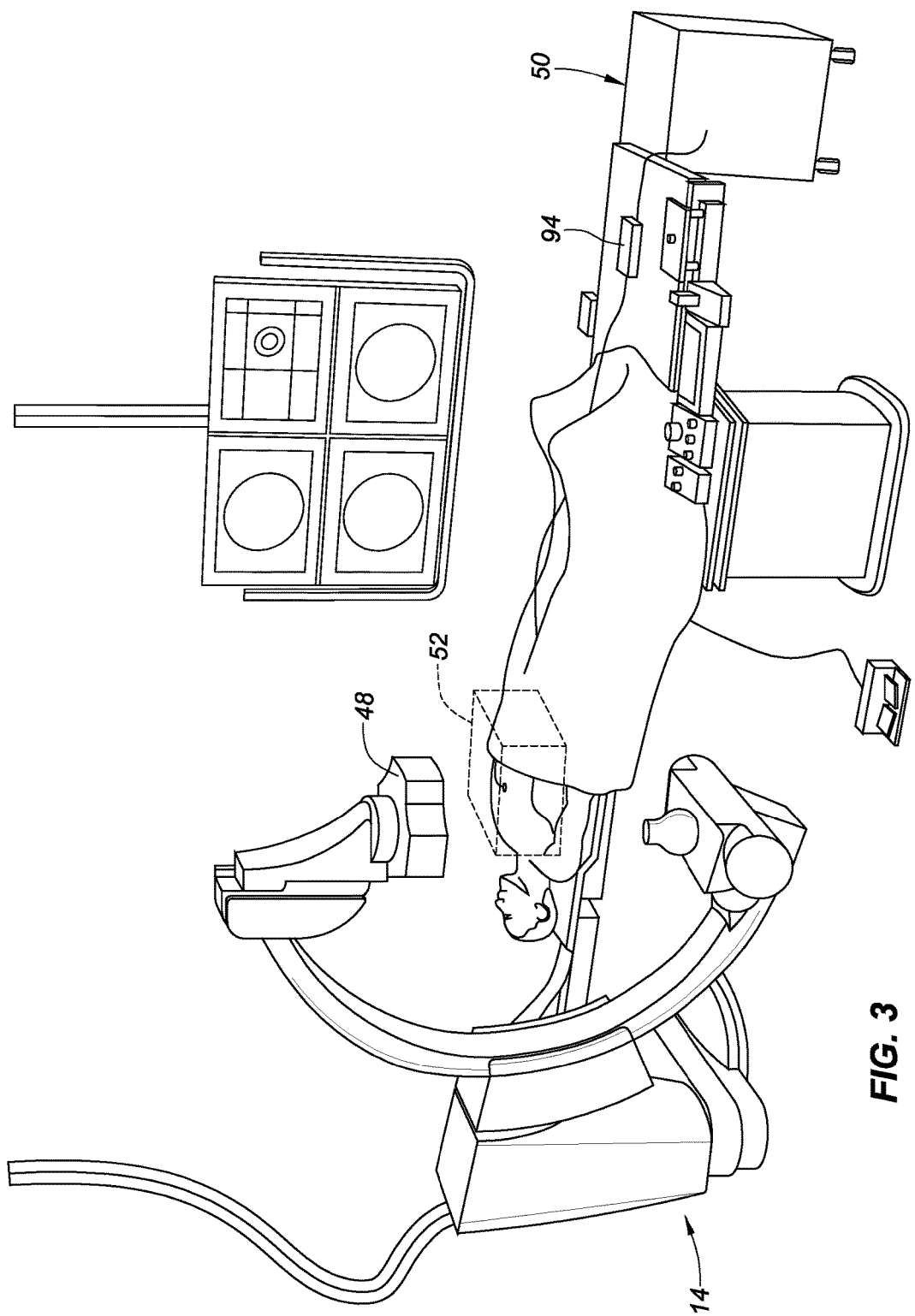
FIG. 3 is a diagrammatic view of a magnetic field-based medical positioning system configured for use in the system illustrated in FIG. 1, in accordance with embodiments of the present disclosure.

With reference to FIGS. 1 and 3, the medical positioning system 14 will now be described. FIG. 3 is a diagrammatic view of a magnetic field-based medical positioning system 14 configured for use in the system illustrated in FIG. 1, in accordance with embodiments of the present disclosure. The medical positioning system 14 is provided for determining the P&O of the sensor 28 of the catheter 12, and thus, the P&O of the catheter 12. In one embodiment, the medical positioning system 14 may comprise a magnetic field-based system such as, for example, the Carto™ System available from Biosense Webster, and as generally shown with reference to one or more of U.S. Pat. Nos. 6,498,944; 6,788,967; and 6,690,963, the entire disclosures of which are incorporated herein by reference, or the MediGuide™ system from MediGuide Ltd. (now owned by St. Jude Medical, Inc.), and as generally shown with reference to one or more of U.S. Pat. Nos. 6,233,476; 7,197,354; and 7,386,339, the entire disclosures of which are incorporated herein by reference. Alternatively, the medical positioning system 14 may comprise a combination magnetic field-based system and electric field-based system such as, for example and without limitation, the Carto 3™ System also available from Biosense Webster.

In one embodiment, and in general terms, the medical positioning system 14 comprises, at least in part, a magnetic transmitter assembly (MTA) 48 and a magnetic processing core 50 for making P&O determinations. The MTA 48 is configured to generate low-strength magnetic field(s) in and around the patient's chest cavity in a predefined three-dimensional space designated as motion box 52 in FIG. 3. In such an embodiment, and as briefly described above, the catheter 12 includes a position sensor 28 comprising a magnetic sensor configured to detect one or more characteristics of the low-strength magnetic field(s) applied by the MTA 48 when the sensor 28 is disposed within the motion box 52. The sensor 28, which in an embodiment comprises a magnetic coil, is electrically connected to the processing core 50 and configured to generate a signal corresponding to the sensed characteristics of the magnetic field(s) that is provided to the magnetic processing core 50. The processing core 50 is responsive to the detected signal and is configured to calculate a three-dimensional P&O reading for the sensor 28. Thus, the medical positioning system 14 enables real-time tracking of each magnetic sensor 28 of the catheter 12 in three-dimensional space, and therefore, real-time tracking of the catheter 12.

Figure 4:
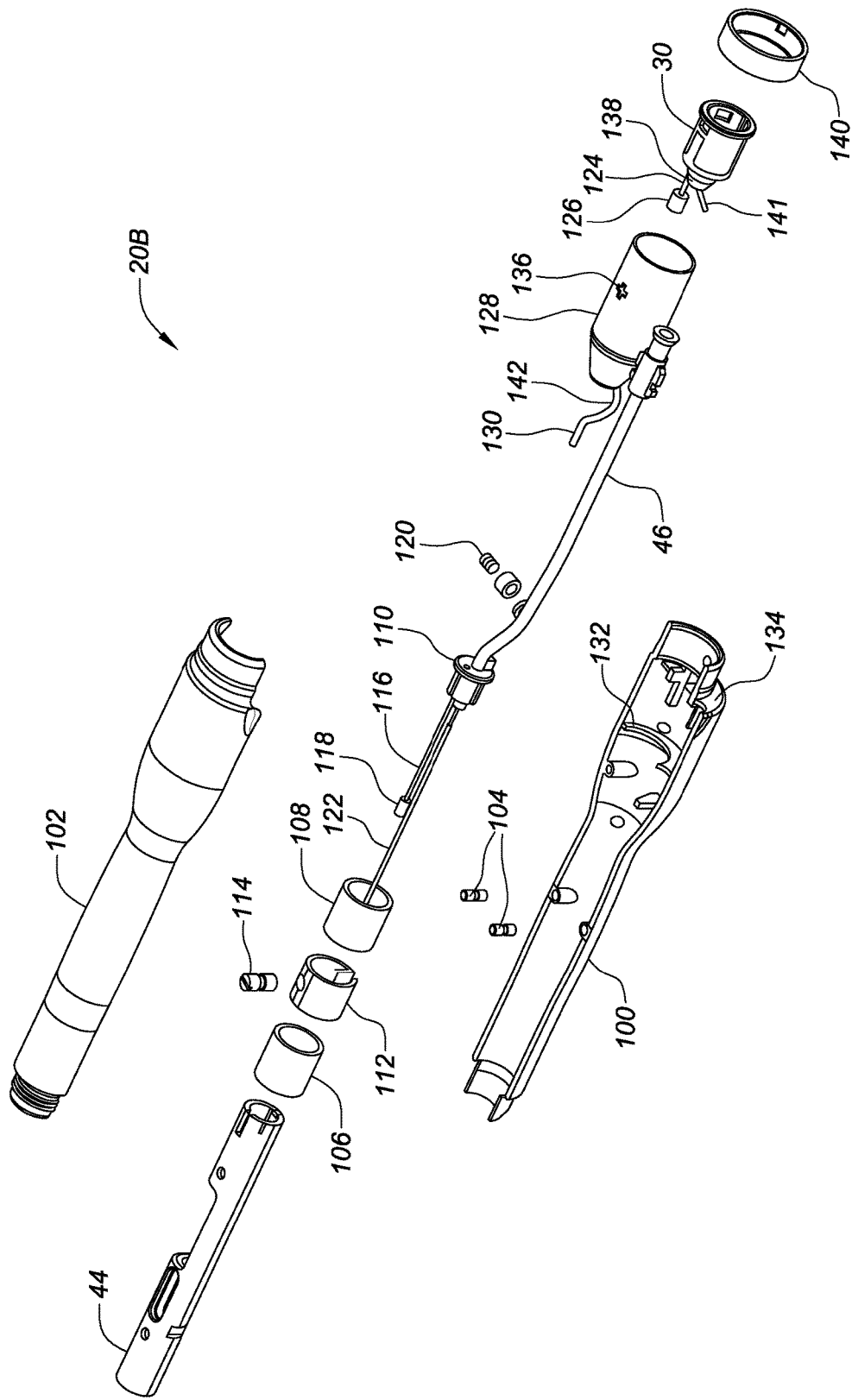
FIG. 4 is an exploded, isometric view of the components comprising the uni-directional catheter actuator depicted in FIG. 2B, in accordance with embodiments of the present disclosure.

FIG. 4 is an exploded, isometric view of the components comprising the catheter actuator 20B depicted in FIG. 2B, in accordance with embodiments of the present disclosure. Various aspects of the catheter actuator 20B are further discussed in US patent publication no. 2015/0094654, which is hereby incorporated by reference as though fully set forth herein. Various internal components of the catheter actuator 20B can be housed in a housing that comprises a lower handle housing 100 and an upper handle housing 102. The lower handle housing 100 and the upper handle housing 102 can be configured to be joined together with an adhesive and/or one or more connectors such as screws or pins (e.g., ferrol pins 104). In some embodiments, the lower handle housing 100 and upper handle housing 102 can be held together by an assembly ring 140.

The housing can include a plunger assembly 44 that extends from a distal end of the housing and can slide distally and proximally out of and in to, respectively, the housing to deflect a distal tip section of the shaft 22, as depicted in FIG. 1. As the plunger assembly 44 is fully advanced from (i.e., pushed distally and fully extended from) the handle housing, an active deflection element 116 (e.g., an active tension member or pull wire or puller wire or tension strand or tension cord or tension fiber) can been fully actuated, thereby fully deflecting the catheter tip section. The deflection element 116 can include a crimp sleeve, which can be configured to engage a gripper 112, discussed below. In some embodiments, the catheter actuator 20B can include a return-to-straight-mechanism 120. Further, as described in relation to FIG. 2B, the catheter actuator can include an irrigation tube 46. A distal irrigation tube portion 122 can extend distally through the handle housing and through the shaft 22 into a distal portion of the shaft 22, in some embodiments. The deflection element 116 and the distal irrigation tube portion 122 have been truncated in FIG. 4 for ease of illustration.

The electromechanical connector 30 can be disposed at a proximal end of the handle housing. For example, the electromechanical connector 30 can be disposed between the lower handle housing 100 and the upper handle housing 102. In some embodiments, the electromechanical connector 30 can be disposed at an end of a pigtail that is located proximally with respect to the handle housing, as discussed herein. As depicted in FIG. 4, the electromechanical connector 30 is a female connector that includes one or more twisted pair(s) 124 electrically coupled to a distal end of the electromechanical connector 30. However, the electromechanical connector 30 can also be another type of connector. The twisted pairs 124 can extend from a sensor located in the distal portion of the shaft 22 to the electromechanical connector 30 and can be housed in a protective conduit 126. The twisted pairs 124 and protective conduit 126 have been truncated in FIG. 4 for ease of illustration. As discussed herein, a proximal end of the twisted pairs 124 can be untwisted and can be terminated at the electromechanical connector 30, where they are electrically coupled to electrical terminals via a connector (e.g., solder 138). The untwisted portion of the twisted pairs 124 can form a loop, causing that portion of the twisted pairs 124 to be susceptible to the magnetic field, thus causing signal noise to be generated. In some embodiments, protective tubing 141 can extend from a distal end of the electromechanical connector 30. In some embodiments, leads for various components located within the catheter (e.g., catheter handle, distal portion of the catheter) can be routed through the protective tubing 141.

Embodiments of the present disclosure can reduce the susceptibility of the untwisted portion to the magnetic field by shielding the untwisted portion of the twisted pairs. Shielding of the untwisted portion can be provided via a connector shield 128. In some embodiments, the connector shield 128 can be an elongate hollow cylinder with a closed distal end (e.g., a can). The connector shield 128 can be formed from a magnetically permeable material, such as mu-metal (e.g., nickel-iron alloy), iron, among other types of magnetically permeable materials. Additional magnetically permeable materials that can form the connector shield can include ferrite, martensitic stainless steel, ferritic stainless steel, electrical steel, permalloy, cobalt-iron, metallic glass (e.g., Metglas®), etc. The magnetically permeable material can provide a low reluctance path for magnetic flux, thus providing a path for magnetic field lines around an area shielded by the connector shield 128. As depicted and discussed herein, the connector shield 128 can be disposed in a proximal portion of the catheter actuator 20B. Further aspects of the connector shield 128 are discussed herein.

In some embodiments, the lower handle housing 100 and the upper handle housing 102 can be configured to house the connector shield 128. In an example, the lower handle housing 100 and/or the upper handle housing 102 can include support ridges 132 that extend from an inner wall of the lower and/or upper handle housing 100, 102 toward a central longitudinal axis defined by the handle housing. The connector shield 128 can be inserted in the proximal end of the handle housing such that a proximal end of the connector shield 128 can abut a proximal wall 134 of the handle housing. In some embodiments, the connector shield 128 can include one or more retention features (e.g., a first retention feature 136), through which corresponding features in the handle housing can pass and serve to retain the connector shield 128 within the handle housing.

In some embodiments, one or more leads (e.g., wires) that connect the one or more sensors located in the distal end of the shaft 22 can pass through a wire management port in the connector shield 128, as further depicted in FIGS. 5A to 5D and can be connected to the connector shield 128 and/or the electromechanical connector 30. As depicted in FIG. 4, the leads can pass through a wire management tube 130, which is connected to the connector shield 128. For example, the wire management tube 130 can be connected with an adhesive applied, or other type of connection, at an interface between the wire management tube 130 and the wire management port in the connector shield 128, such that the wire management tube extends distally from the wire management port. As discussed herein, the plunger assembly 44 can slide distally and proximally out of and in to, respectively, the housing to deflect the distal tip section of the shaft 22. The proximal end of the shaft 22 can be connected to the plunger assembly 44 and thus the handle housing (e.g., lower handle housing 100 and upper handle housing 102), including the electromechanical connector 30 and the connector shield 128, can move with respect to the plunger assembly 44 and the shaft 22. As a result of the respective movement and the fact that the leads are fixed relative to the movement of the shaft 22 and the plunger assembly 44, leads and/or a conduit that houses the leads can be tensioned. For example, as the plunger assembly 44 is moved distally out of the handle housing, the leads can be tensioned; and as the plunger assembly 44 is moved proximally in to the handle housing, slack can be created in the leads. If a sufficient amount of slack does not exist in the leads, when the plunger assembly 44 (and shaft 22) is moved distally out of the handle housing, a sufficient amount of tension can be created in the leads to cause a break to occur in the leads. Accordingly, embodiments of the present disclosure can include a service loop, which provides a controllable component that includes a built in amount of slack.

In an example, the wire management tube 130 can include a service loop 142 that forms a non-linear (e.g., bent, helical, zig-zagged, etc.) path through which the leads can pass. Accordingly, as the plunger assembly 44 is moved distally out of the handle housing, and tension is created in the leads, the non-linear path formed by the service loop can straighten (e.g., deform from a biased state), allowing for a linear length of leads between the electromechanical connector 30 and the sensor to lengthen. In some embodiments, the service loop 142 can be biased to include the non-linear path. For example, the service loop 142 can be formed such that the service loop 142 is naturally biased to include the non-linear path. As a result, a manufacturing consistency can be introduced when assembling the catheter. For example, previous methods for assembling catheters have involved a user building some slack into the leads, when assembling the catheter. However, inevitably, the amount of slack built into the leads can vary from actuator to actuator. As a result of building in an inadequate amount of lead slack into the catheter, the leads can become tensioned to a point where a break occurs in the leads and/or conduit housing the leads. Accordingly, embodiments of the present disclosure can resolve the issue of building in varying amounts (e.g., inadequate amounts) of lead slack into the catheter. As the leads are tensioned, the service loop 142 can be pulled and straightened by the leads, relieving the tension in the leads and preventing a break from occurring in the leads and/or conduit housing the leads.

Figure 5C:
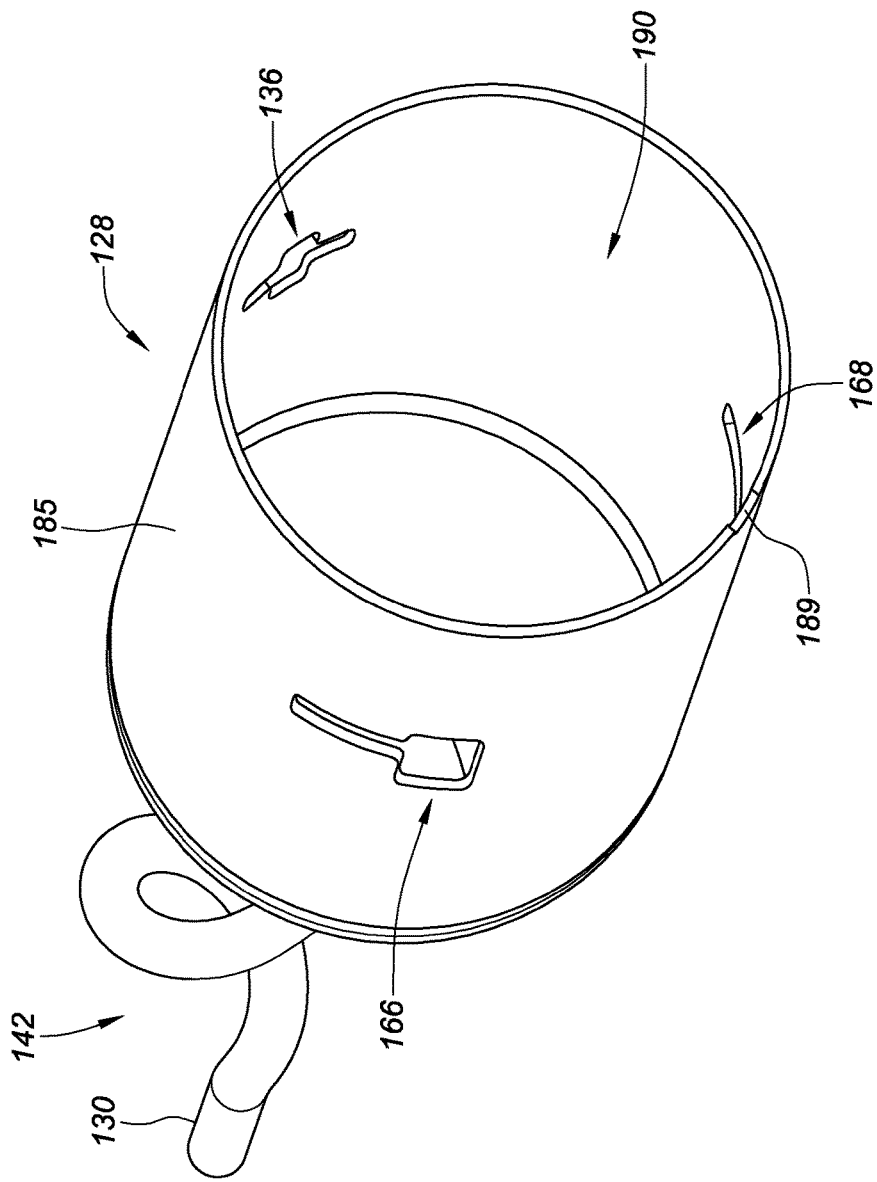
FIG. 5C is an isometric side and proximal view of the connector shield and wire management tube depicted in FIG. 5A, in accordance with embodiments of the present disclosure.

FIG. 5A is a side view of a connector shield 128 and a wire management tube 130, as depicted in FIG. 4, in accordance with embodiments of the present disclosure. In some embodiments of the present disclosure, the connector shield 128 can include an elongate hollow cylindrical body 185 that extends along a longitudinal axis a-a. The connector shield can include a distal cap portion 163 that extends along the longitudinal axis a-a, a proximal end of which can be connected to a distal end of the elongate hollow cylindrical body. The distal cap portion 163 can include an elongate hollow distal portion that extends along the longitudinal axis a-a. In an example, a proximal end of the elongate hollow distal portion can be connected to a distal end of the elongate hollow cylindrical body 185. In some embodiments, a distal face can be connected to a distal end of the elongate hollow distal portion. In some embodiments, the elongate hollow distal portion can be frustoconical in shape, although the elongate hollow distal portion can be formed as other shapes, as discussed herein. For example, embodiments, of the present disclosure can include a frustoconical distal portion 186 that includes a closed distal end 160. The frustoconical distal portion 186 and closed distal end 160 along with the elongate hollow cylindrical body 185 form the connector shield 128, which extends along the longitudinal axis a-a. However, in some embodiments, the distal portion can be of another shape, as further discussed herein. The connector shield 128 can define a lumen 190, as depicted in FIG. 5C. In an example, a proximal end 162 of the connector shield 128 can have an opening, a diameter of which can be defined by a proximal end of the inner walls of the elongate hollow cylindrical body 185, further depicted in FIG. 5C.

In some embodiments, the connector shield 128 can include a wire management port 164 extending through a wall of the connector shield 128. In some embodiments, the wire management port 164 can be defined in the distal cap portion 163. The wire management port 164 can be disposed at a location on the connector shield 128 that is off-axis with respect to the longitudinal axis a-a. For example, as depicted in FIG. 5A, the wire management port 164 can be defined in a sidewall of the frustoconical distal portion 186 that is off-axis with respect to the longitudinal axis a-a. Although the wire management port 164 is depicted as being disposed on an upper distal half of the frustoconical distal portion 186 of the connector shield 128, the wire management port 164 can be disposed at other locations on the frustoconical distal portion 186. For example, the wire management port 164 can be disposed at an axial middle of the frustoconical distal portion 186 or on a lower proximal half of the frustoconical distal portion 186. In some embodiments, the wire management port 164 can be advantageously disposed on the upper distal half of the frustoconical distal portion 186 of the connector shield 128. For example, by disposing the wire management port 164 on the upper distal half of the frustoconical distal portion 186, the wire management tube 130 can exit the wire management port 164 and have sufficient room to turn distally towards the shaft 22 (FIG. 1) and away from the connector shield 128. For instance, as depicted in FIG. 5A, the wire management tube 130 extends from the wire management port 164 and makes a turn towards the shaft 22 and away from the connector shield 128 all while residing within a profile of the elongate hollow cylindrical body 185 of the connector shield 128.

In some embodiments, as discussed herein, the wire management tube 130 can include a service loop 142 having an axial length defined by line b-b in a naturally biased state. The service loop 142 can include a built in amount of slack to account for the distal movement of the plunger assembly out of the handle housing and the tensioning of the leads. In some embodiments, for example, the service loop 142 can provide a non-linear path through which the leads travel. As tension is applied to the service loop 142 and/or leads, the service loop can straighten (e.g., deform from the naturally biased state), causing an amount of tension in the leads and/or an associated conduit through which the leads pass to remain below a particular threshold. For example, the axial length of the service loop 142 in the naturally biased state, defined by line b-b, can increase to an axial length greater than that defined by line b-b in a tensioned state. Thus, damage to the leads and/or the conduit that carries the leads can be prevented when the service loop axially lengthens, introducing slack into the system. In some embodiments, the wire management tube 130 can be formed from a flexible material. For example, the wire management tube 130 can be formed from a metal (e.g., nitinol), a polymer (e.g., PEBAX), etc.

In some embodiments, the connector shield 128 can include retention features 136, 166, 168. As discussed herein, the connector shield 128 can include retention features 136, 166, 168, through which corresponding features in the handle housing can pass and serve to retain the connector shield 128 within the handle housing. In some embodiments, one or more features included in the handle housing can pass through the retention features 136, 166, 168 and contact the electromechanical connector 30 to retain the electromechanical connector 30 within the connector shield 128 and within the handle housing.

In some embodiments, the electromechanical connector 30 can be inserted within a lumen formed by the connector shield 128. For example, a distal end of the electromechanical connector 30 can be inserted into the lumen formed by the connector shield 128 and features included on the handle housing can pass through the retention features 136, 166, 168, and contact the electromechanical connector 30 to retain the electromechanical connector 30 or a portion of the electromechanical connector 30 within the connector shield and/or the handle housing. In some embodiments, a longitudinal axis of the electromechanical connector 30 can align with a longitudinal axis of the connector shield 128.

In some embodiments, the retention features can be thru-holes that extend through a side wall of the elongate hollow cylindrical body 185. With respect to a second retention feature 166, the second retention feature 166 can include a first rectangular thru-hole 170 that extends axially along a sidewall of the elongate hollow cylindrical body 185 and a second thru-hole 172 that extends circumferentially from the first rectangular thru-hole 170. A third retention feature 168 can include a first rectangular thru-hole 174 that extends axially along the sidewall of the elongate hollow cylindrical body 185 and a second thru-hole 176 that extends circumferentially in an opposite or same direction as the second thru-hole 172 of the first retention feature 166. In some embodiments, edges along the perimeter of the retention features 136, 166, 168 (e.g., perimeter edge 187) can be radiused to prevent a disturbance in a magnetic field passing over the retention features 136, 166, 168.

In some embodiments, the connector shield 128 can include an alignment feature 189. The alignment feature 189 can be configured to enable the connector shield 128 to be positioned in a catheter actuator in a particular orientation. For example, in some embodiments, the catheter actuator (e.g., catheter actuator 20B) can include a corresponding alignment feature that is configured to engage the alignment feature 189. In some embodiments, and as depicted, the alignment feature 189 can be a semicircular cutout formed in a proximal end of the elongate hollow cylindrical body 185. However, the alignment feature 189 can be a square cutout, rectangular cutout, triangular cutout, etc. In some embodiments, an alignment feature can be formed on a sidewall of the connector shield 128 (e.g., an indent or radially extending feature can be formed on a sidewall of the elongate hollow cylindrical body 185) or through a sidewall of the connector shield 128 (e.g., a hole can be formed in a sidewall of the elongate hollow cylindrical body 185).

FIG. 5B is an isometric side and distal view of the connector shield 128 and the wire management tube 130 depicted in FIG. 5A, in accordance with embodiments of the present disclosure. In some embodiments, the closed distal end 160 of the frustoconical distal portion 186 can include a distal cap portion 180 connected to the distal end of the frustoconical distal portion 186, which can serve to close off a distal opening in the frustoconical distal portion 186. A distal surface of the distal cap portion 180 can be oriented along a plane that is transverse to the longitudinal axis a-a.

The distal cap portion 180 can be formed from a thicker material than other areas of the connector shield 128, in some embodiments.

In an example, the closed distal end 160 (e.g., distal face) of the connector shield 128 can be oriented towards a magnetic field generator, potentially causing the closed distal end 160 to be impacted by a stronger field than other portions of the connector shield 128. Thus, forming the distal cap portion 180 from a magnetically permeable material that is thicker than other portions of the connector shield 128 (e.g., frustoconical distal portion 186, elongate hollow cylindrical body 185) can be beneficial in preventing the distal cap portion 180 from being oversaturated with flux, causing an overflow of flux to enter a lumen formed by the connector shield 128.

In some embodiments, the frustoconical distal portion 186 can be formed of a magnetically permeable material that has a greater thickness than the elongate hollow cylindrical body 185. In an example, the frustoconical distal portion 186 can be formed from a magnetically permeable material that has a similar or same thickness as the distal cap portion 180. Because the frustoconical distal portion 186 is located closer to the magnetic field generator, a stronger field can impact the frustoconical distal portion 186. Thus, use of a thicker magnetically permeable material in the frustoconical distal portion 186 can prevent the frustoconical distal portion 186 from being oversaturated with flux. In addition, the distal cap portion 180 and the frustoconical distal portion 186 can be more directly impacted by the magnetic field because their surfaces may not be parallel to magnetic field lines produced by the magnetic field generator. As such, the magnetic field may impact those portions of the connector shield more so than the elongate hollow cylindrical body 185, which includes side walls that can generally be parallel to magnetic field lines produced by the magnetic field generator. Generally a thickness of the material forming the various portions of the connector shield 128 can be of sufficient thickness to prevent flux saturation and flux lines from passing through the material to the shielded components.

With further reference to FIG. 5A, a first edge 182 between the closed distal end 160 and the frustoconical distal portion 186 can be radiused, which can cause the magnetic field to pass smoothly over the first edge 182, and may not disrupt the magnetic field. In addition, a second edge 184 between the frustoconical distal portion 186 and the elongate hollow cylindrical body 185 can be radiused to cause the magnetic field to pass smoothly over the second edge 184 and not disrupt the magnetic field.

FIG. 5C is an isometric side and proximal view of the connector shield 128 and wire management tube 130 depicted in FIG. 5A, in accordance with embodiments of the present disclosure. As depicted, the connector shield 128 can define a lumen 190 that extends through a center of the elongate hollow cylindrical body 185 and into the frustoconical distal portion 186. In some embodiments, as discussed herein, the elongate hollow cylindrical body 185 can be sized and configured to house the electromechanical connector 30. For example, the electromechanical connector 30 can be disposed within the lumen 190. The untwisted portion of the twisted pair can be housed within the lumen 190 and electrically coupled to the electromechanical connector 30.

Figure 5D:
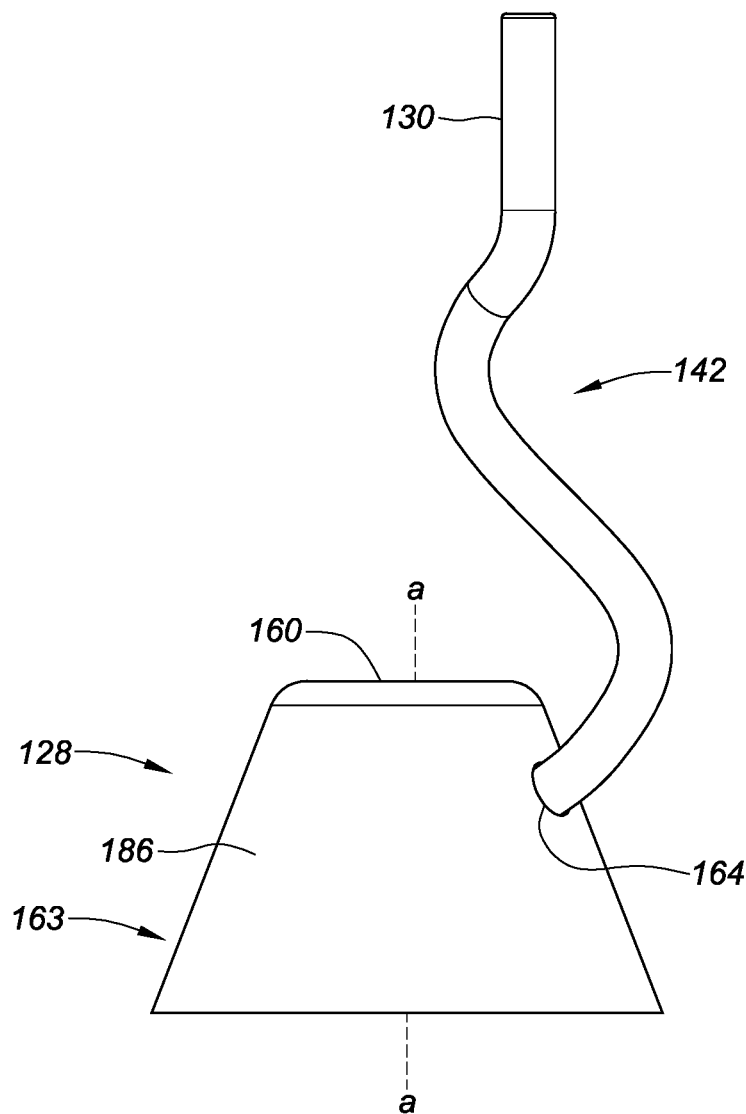
FIG. 5D is a side view of a frustoconical distal portion of the connector shield and wire management tube depicted in FIG. 5A, in accordance with embodiments of the present disclosure.

FIG. 5D is a side view of a frustoconical distal portion 186 of the connector shield 128 and wire management tube 142 depicted in FIG. 5A, in accordance with embodiments of the present disclosure. In some embodiments, the wire management port 164 can be a circular port that is defined in the frustoconical distal portion 186. The wire management port 164 can extend through the frustoconical distal portion 186 of the connector shield 128 and the wire management tube 142 can extend from the wire management port 164 at a non-zero angle with respect to the longitudinal axis a-a. For example, a proximal end of the wire management tube 142 may not be parallel to the longitudinal axis a-a. In some embodiments, the wire management port 164 can be oblong, having a longer axial width than circumferential width. Accordingly, a proximal end of the wire management tube 142 can pass through the wire management port 164 in a more parallel relationship to the longitudinal axis a-a.

In some embodiments, edges of the frustoconical distal portion 186 that define the wire management port 164 can be radiused to prevent abrasion of the wire management tube 142, leads passing through the wire management tube 142, and/or insulation covering the leads. In some embodiments, a grommet can be disposed in the wire management port 164 to prevent the wire management tube 142 and/or leads from contacting the edges that define the wire management port 164; thus preventing abrasion of the wire management tube 142 and/or leads. In some embodiments, the surface of the connector shield 128, including the edges that define the wire management port 164 can be smoothed via polishing (e.g., electropolishing), to reduce and/or eliminate abrasion between the wire management tube 142 and/or leads and the edges that define the wire management port 164. In some embodiments, an eyelet can be disposed in the wire management port 164, which can cover the edges of the connector shield 128 that define the wire management port 164. In an example, the eyelet can be formed from a metal such as aluminum.

Figure 5E:
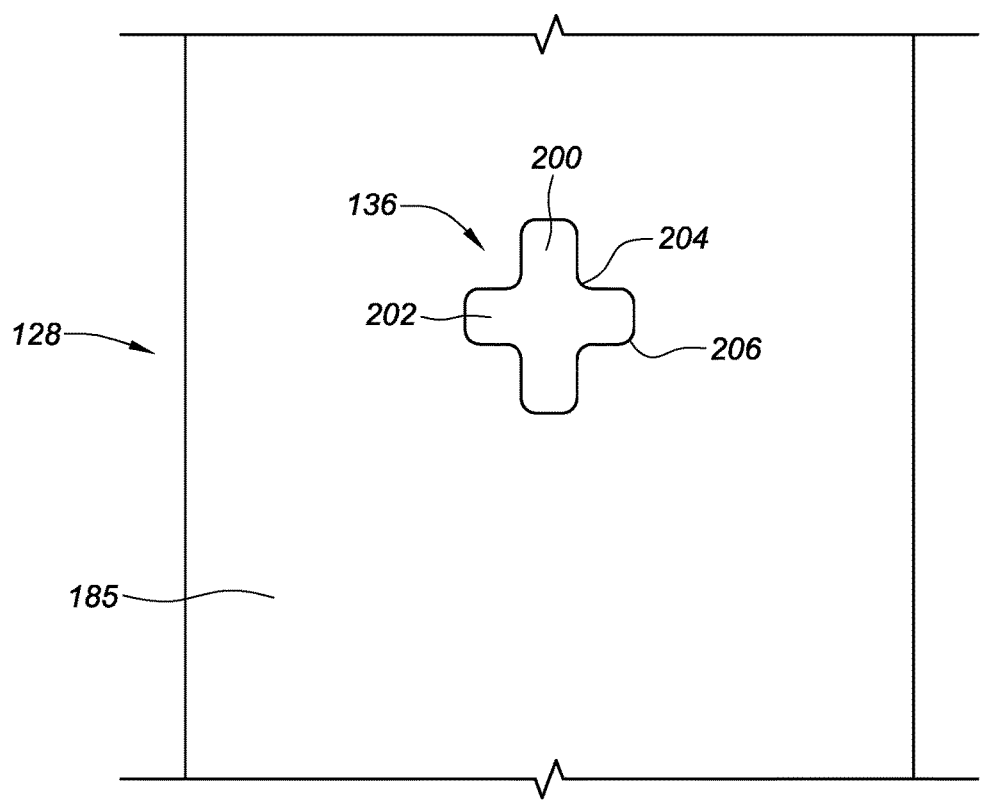
FIG. 5E depicts a retention feature included on the connector shield depicted in FIG. 5A, in accordance with embodiments of the present disclosure.

FIG. 5E depicts a retention feature 136 included on the connector shield 128 depicted in FIG. 5A, in accordance with embodiments of the present disclosure. The retention feature 136 can include a first rectangular thru-hole 200 that extends axially along a sidewall of the elongate hollow cylindrical body 185 and a second rectangular thru-hole 202 that extends circumferentially through a middle of the first rectangular thru-hole 200. In some embodiments, as depicted, areas where the first rectangular thru-hole 200 and the second rectangular thru-hole 202 intersect (e.g., corner edge 204), can be radiused (e.g., rounded, smoothed). In some embodiments, edges along an entire outer and/or inner perimeter (e.g., perimeter edges) of the thru-holes can be radiused, as previously discussed. In an example, the radiused edges can prevent or reduce a disturbance to an applied magnetic field when the field contacts the edges. In some embodiments, the radiused edges can cause a magnetic field to pass smoothly over the edge and may not disrupt the magnetic field. In contrast, an un-radiused edge may cause the field to act unpredictably and be directed through the thru-hole and into an inner lumen of the connector shield 128. As depicted in FIG. 5E, in addition, corners of each of the thru-holes (e.g., corner 206) can be radiused to prevent or reduce a disturbance to the applied magnetic field, as discussed in relation to the points of intersection between the thru-holes. In some embodiments, although the retention feature 136 is depicted as including first and second rectangular thru-holes, the retention feature 136 can be a circular, oblong, rectangular, square, triangular, and/or polygonal thru-hole.

Figure 6A:
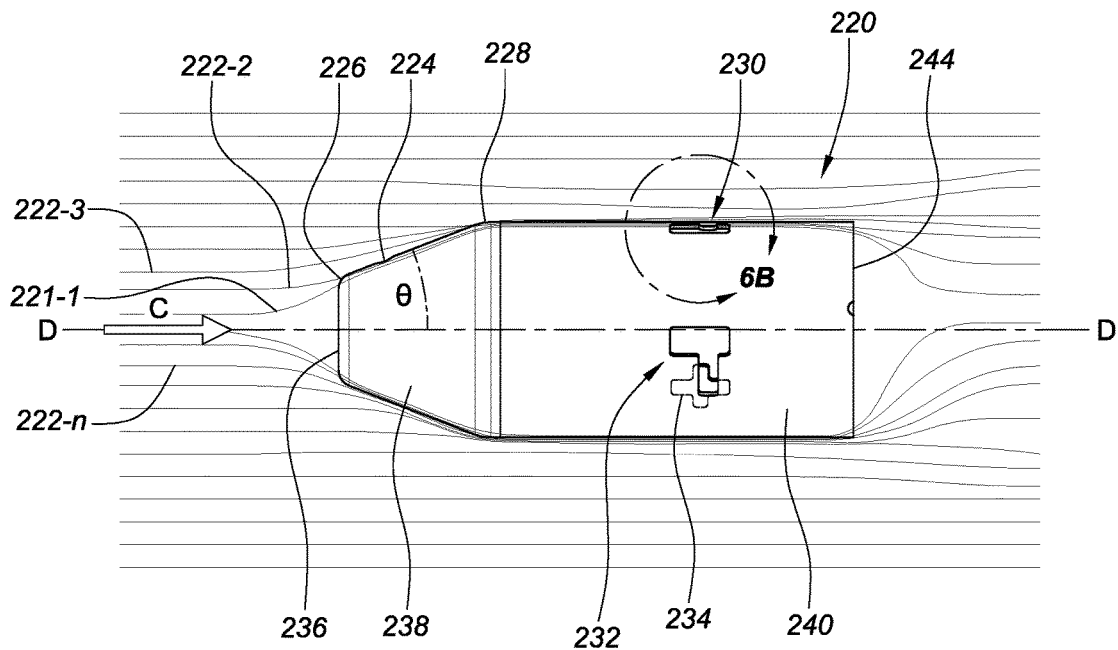
FIG. 6A is a side view of a connector shield in relation to magnetic field lines, in accordance with embodiments of the present disclosure.
Figure 6B:
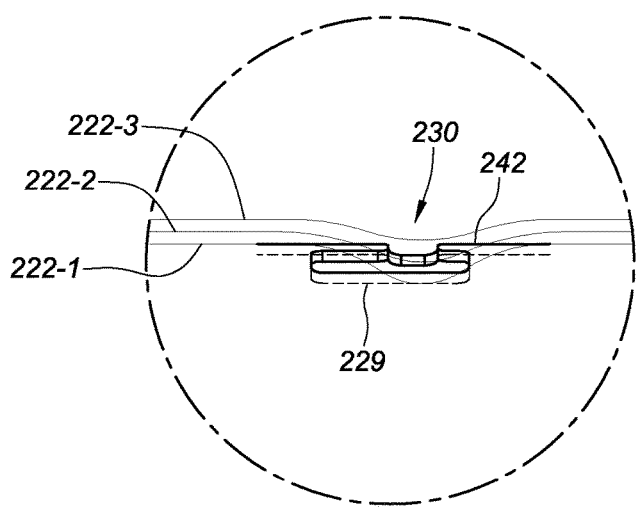
FIG. 6B is an enlarged side view of a retention feature included on the connector shield depicted in FIG. 6A in relation to magnetic field lines, in accordance with embodiments of the present disclosure.

FIG. 6A is a side view of a connector shield 220 in relation to magnetic field lines (e.g., magnetic field lines 222-1, 222-2, 222-3, 222-n, hereinafter generally referred to in the plural as magnetic field lines 222), in accordance with embodiments of the present disclosure. The connector shield 220 can include a first retention feature 234 (shown in phantom), a second retention feature 230, and a third retention feature 232, as well as radiused edges 226, 228, as discussed herein. FIG. 6B is an enlarged side view of the second retention feature 230 included on the connector shield 220 depicted in FIG. 6A in relation to magnetic field lines 222, in accordance with embodiments of the present disclosure.

The connector shield 220 can include a wire management port 224, disposed on the frustoconical distal portion 238 and off-axis with respect to a longitudinal axis D-D that passes through the connector shield 220. In some embodiments, disposing the wire management port 224 off-axis with respect to the longitudinal axis D-D of the connector shield 220 can prevent the magnetic field from entering the wire management port 224 and thus entering the lumen defined by the connector shield 220. As depicted and discussed herein, because the connector shield 220 can generally be oriented toward a source of the magnetic field (e.g., originating from a source in a direction opposite of arrow C), magnetic field lines can generally travel parallel to the longitudinal axis D-D of the connector shield 220.

As the magnetic field lines 222 approach the connector shield, the magnetic field lines 222 can be split at the closed distal end 236. If the wire management port were placed on the longitudinal axis D-D of the connector shield 220, the magnetic field lines 222 can be more likely to enter the connector shield 220 via the on-axis wire management port. For example, as illustrated in FIG. 6A, because the closed distal end 236 of the connector shield 220 is in fact closed and no entry points exist in the closed distal end 236, the magnetic field lines 222 can be directed around the closed distal end 236, as depicted in FIG. 6A. If a wire management port or other type of port and/or hole were included on the longitudinal axis D-D on the distal end of the connector shield 220, the magnetic field lines could be more likely to enter the port and/or hole and pass into the lumen defined by the connector shield 220.

As such, embodiments of the present disclosure can include an off-axis wire management port disposed on the connector shield 220. For instance, as depicted in FIG. 6A, the wire management port 224 is disposed off-axis with respect to the longitudinal axis D-D on a sidewall of the frustoconical distal portion 238. Thus, the magnetic field lines can be more likely to pass over the wire management port 224. In some embodiments, the sidewall of the frustoconical distal portion 238 can be at an angle (Θ) with respect to the longitudinal axis D-D. In some embodiments, the angle Θ can be configured to limit an amount of magnetic flux that enters a lumen of the connector shield 220. In some embodiments, forming the sidewall of the frustoconical distal portion 238 at an angle can reduce a chance that the magnetic field will enter the wire management port 224 disposed on the sidewall. In an example, as an angle of the sidewall of the frustoconical distal end with respect to the longitudinal axis decreases, the magnetic field can be less likely to enter the wire management port 224. For instance, the magnetic field can more easily pass over the wire management port 224.

In some embodiments, as discussed herein, a magnetic field generator can be located distally with respect to the connector shield 220 and can generate a magnetic field, which can pass over the connector shield 220 in the direction of arrow C. In some embodiments, the connector shield 220 can include radiused edges. For example, with reference to FIG. 5A, a first edge 226 between a closed distal end 236 and the frustoconical distal portion 238 can be radiused, which can cause the magnetic field lines 222 to pass smoothly over the first edge 226, and may not disrupt the magnetic field. As previously discussed, the magnetic field lines 222 can pass over the wire management port 224 disposed on the sidewall of the frustoconical distal portion 238. In some embodiments, a second edge 228 between the frustoconical distal portion 238 and the elongate hollow cylindrical body 240 can be radiused to cause the magnetic field lines 222 to pass smoothly over the second edge 228 and not disrupt the magnetic field. For example, with respect to FIG. 6A, the magnetic field line 222-1 can smoothly pass over the connector shield 220 without significant disturbance to the magnetic field line 222-1. For instance, the magnetic field line 222-1 can pass over the first radiused edge 226, the wire management port 224, and the second radiused edge 228.

In some embodiments, the size of the wire management port 224 (e.g., diameter) can be made small to prevent the magnetic field from entering the wire management port 224. In an example, as a size of the wire management port 224 is reduced, a likelihood that the magnetic field will enter the wire management port 224 can also be reduced. Accordingly, a size of the wire management port 224 can be configured to limit an amount of magnetic flux that enters a lumen of the connector shield 220.

In some embodiments, the magnetic field lines 222 can pass over the retention features (e.g., second retention feature 230). FIG. 6B is in more detail a side view of the second retention feature 230 included on the connector shield 220 depicted in FIG. 6A in relation to the magnetic field lines 222, in accordance with embodiments of the present disclosure. As depicted, a first magnetic field line 222-1 can enter the retention feature 230. In some embodiments, the first magnetic field line 222-1 can be drawn back out of the retention feature 230 by a magnetically permeable sidewall in which the retention feature 230 is formed. In some embodiments, as a thickness of the magnetically permeable sidewall increases, the magnetic field can be less likely to enter the retention features. An inner sidewall 229 of the magnetically permeable sidewall is depicted in phantom. If the magnetic field enters the retention feature 230, the field can be drawn into the shield, as depicted in FIG. 6B. For example, the magnetically permeable material forming the sidewall 242 of the connector shield 220 can draw the magnetic field lines 222-1, 222-2 that have entered the retention feature 230 back into the sidewall 242 of the connector shield 230. In some embodiments, a largest dimension of the retention feature (e.g., circumferential dimension, axial dimension) can be configured to limit an amount of magnetic flux that enters a lumen formed by the connector shield 220.

With further reference to FIG. 6A, as the magnetic field lines 222 pass over the connector shield 220 and past a proximal end 244 of the connector shield 220. The magnetic field lines 222 can be directed away from the proximal end 244 and the lumen defined by the connector shield 220. In some embodiments, the magnetic field lines 222 can be directed away from the proximal end 244 and the lumen defined by the connector shield 220 because the proximal end 244 of the connector shield 220 is generally directed away from the magnetic field generator during a procedure.

Figure 6C:
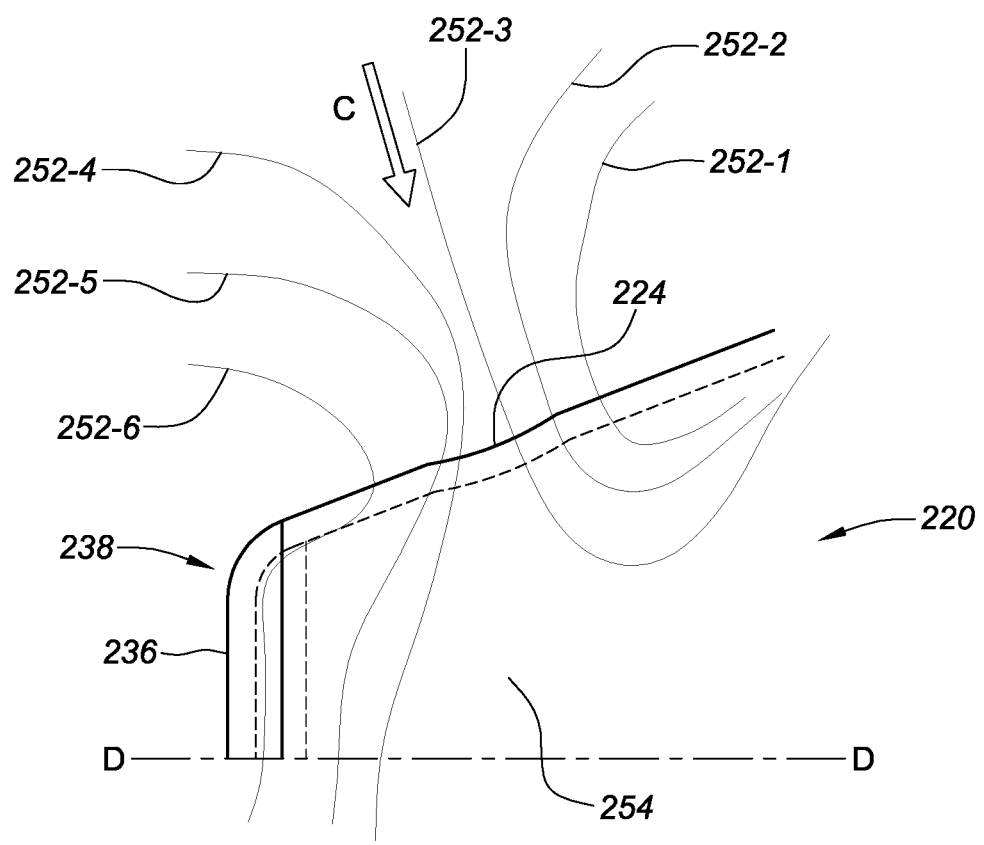
FIG. 6C is an enlarged, fragmentary, cross-sectional view of a portion of the frustoconical distal portion of the connector shield depicted in FIG. 6A, and depicts magnetic field lines in and around a wire management port, in accordance with embodiments of the present disclosure.

FIG. 6C is an enlarged, fragmentary, cross-sectional view of a portion of the frustoconical distal portion 238 of the connector shield 220 depicted in FIG. 6A, and depicts magnetic field lines 252-1, 252-2, . . . , 252-6 (generally referred to hereinafter as magnetic field lines 252) in and around a wire management port 250, in accordance with embodiments of the present disclosure. In some embodiments, the connector shield 220 can be positioned such that the magnetic field lines 252 are directed at the connector shield 220 from a different angle. For example, while the magnetic field lines 252 may still originate from a same location and be directed in a same direction (e.g., arrow C), the magnetic field lines 252 may be directed generally perpendicular to a sidewall of the frustoconical distal portion 238.

As depicted, the magnetic field lines 252-2, 252-3, 252-4, 252-5 can enter the wire management port 224. Although the magnetic field lines 252-2, 252-3, 252-4, 252-5 are depicted as entering a lumen 254 defined by the frustoconical distal portion 238, the magnetic field represented by the magnetic field lines 252-2, 252-3, 252-4, 252-5 can be drawn into and/or towards a magnetically permeable material that forms the closed distal end 236 and/or a magnetically permeable material that forms the sidewall of the frustoconical distal portion 238. In an example, the magnetically permeable material that forms the closed distal end 236 and the sidewall of the frustoconical distal portion 238 can have a particular thickness, which can be configured to allow for the magnetic field, represented by the magnetic field lines 252-2, 252-3, 252-4, 252-5, to be drawn towards and/or drawn into the magnetically permeable material and away from a central portion of the lumen 254 defined by the frustoconical distal portion 238 that houses the untwisted portion of the twisted pair. An inner sidewall of the frustoconical distal portion 238 and closed distal end 236 is depicted in phantom. Thus, the untwisted portion shielded by the frustoconical distal portion may not be affected by the magnetic field. In some embodiments, as discussed herein, the diameter of the wire management port 224 can be sized to limit or prevent the magnetic field from entering the lumen 245.

FIGS. 7A to 7D depict side views of connector shields with various profiles, in accordance with embodiments of the present disclosure. In some embodiments, a connector shield comprises different distal end portions. For example, as depicted in FIG. 7A, a conical connector shield 270 can include an elongate hollow cylindrical body 272 with a conical distal portion 274. In some embodiments, a conical distal portion 274 can be particularly effective at redirecting a magnetic field around the conical connector shield 270 as a result of a distal end 276 of the conical connector shield 270 being pointed. In some embodiments, a wire management port can be disposed off of a longitudinal axis E-E associated with the conical connector shield 270 and defined in the conical distal portion 274 and/or in the elongate hollow cylindrical body 272.

As depicted in FIG. 7B, a radiused elongate hollow cylindrical connector shield 280 can include an elongate hollow cylindrical body 282 with a radiused distal portion 284. For example, the radiused distal portion 284 can include radiused distal edges (e.g., radiused distal edge 286) that can prevent and/or reduce disturbances in the magnetic field as it passes over the radiused elongate hollow cylindrical connector shield 280. In some embodiments, a wire management port can be disposed off of a longitudinal axis F-F associated with the radiused connector shield 280 and defined in the radiused distal portion 284 and/or in the elongate hollow cylindrical body 282.

As depicted in FIG. 7C, a domed elongate hollow cylindrical connector shield 290 can include an elongate hollow cylindrical body 292 with a domed distal portion 294, which can prevent and/or reduce disturbances in the magnetic field as it passes over the domed elongate hollow cylindrical connector shield 290. In some embodiments, a wire management port can be disposed off of a longitudinal axis G-G associated with the domed connector shield 290 and defined in the domed distal portion 294 and/or in the elongate hollow cylindrical body 292.

As depicted in FIG. 7D, an elongate hollow cylindrical connector shield 300 can include an elongate hollow cylindrical body 302 with an elongate hollow cylindrical distal portion 304. In some embodiments, the elongate hollow cylindrical distal portion 304 can have 90 degree edges 306. To account for any disturbance caused by the 90 degree edges 306 in the magnetic field, the elongate hollow cylindrical connector shield 300 can be formed from a thicker magnetically permeable material. For example, the magnetically permeable material can have a thickness that is configured to limit an amount of magnetic flux that enters a lumen formed by the connector shield, in some embodiments. In some embodiments, a wire management port can be disposed off of a longitudinal axis H-H associated with the elongate hollow cylindrical connector shield 300 and defined in the elongate hollow cylindrical distal portion 304 and/or in the elongate hollow cylindrical body 302. In some embodiments, the wire management port can be defined in a distal face of the elongate hollow cylindrical distal portion 304 or in a circumferential face of the elongate hollow cylindrical distal portion 302.

Figure 8:
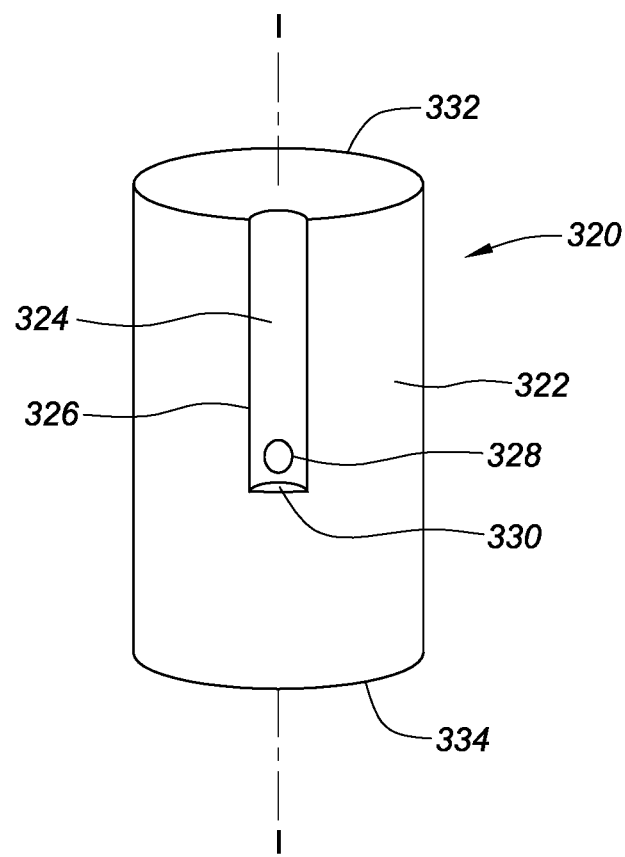
FIG. 8 is an isometric side and distal view of an alternative embodiment of a connector shield, in accordance with embodiments of the present disclosure.

FIG. 8 is an isometric side and distal view of an alternative embodiment of a connector shield, in accordance with embodiments of the present disclosure. As depicted in FIG. 8, the connector shield 320 can include an elongate hollow cylindrical body 322. In some embodiments, the elongate hollow cylindrical body 322 may comprise the entire connector shield, for example, as depicted in FIG. 7D. In other embodiments, the elongate hollow cylindrical body 322 can include a distal portion (e.g., frustoconical, conical, radiused, domed, etc.). In some embodiments, the elongate hollow cylindrical body 322 can include an axial groove 324, channel, or recessed feature extending along a length of a sidewall 326 of the elongate hollow cylindrical body 322. If the connector shield includes a distal portion (e.g., frustoconical, conical, radiused, domed, etc. portion) the distal portion can include a complimentary groove, channel or recessed feature.

In some embodiments, a wire management tube, as previously discussed herein can be disposed within the groove 324 and a wire management port 328 can be located in the groove 324. In some embodiments, a wire management port can be disposed on a base portion 330 of the groove 324. The wire management tube can be connected to an interface between the wire management port (e.g., wire management port 328) and the wire management tube, in some embodiments. As depicted, a surface of the base portion 330 can form a plane that is transverse to the longitudinal axis E-E of the connector shield 320. However, the surface of the base portion 330 can be disposed at an angle (e.g., sloped) with respect to the longitudinal axis I-I (e.g., sloped proximally and away from the longitudinal axis I-I). This can reduce a disturbance to a magnetic field passing from a distal end 332 to a proximal end 334 of the connector shield 320 and reduce an amount of magnetic flux that enters the connector shield.

Embodiments are described herein of various apparatuses, systems, and/or methods. Additional aspects of the present disclosure will be made apparent upon review of the material in Appendix A, attached herewith. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it may be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for a catheter shield for sensor enabled devices has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and may include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device connector shield, comprising:
    an elongate hollow cylindrical body that extends along a longitudinal axis;
    a distal cap portion that extends along the longitudinal axis, wherein a proximal end of the distal cap portion is connected to a distal end of the elongate hollow cylindrical body;
    a wire management port defined in the distal cap portion; and
    a wire management tube extending from the wire management port, wherein the wire management tube extends distally from the wire management port.

2. The medical device connector shield of claim 1, wherein the elongate hollow cylindrical body and the distal cap portion are formed from a magnetically permeable material.

3. The medical device connector shield of claim 1, wherein the wire management tube includes a service loop.

4. The medical device connector shield of claim 1, wherein the distal cap portion further comprises:
    an elongate hollow distal portion that extends along the longitudinal axis, wherein a proximal end of the elongate hollow distal portion is connected to a distal end of the elongate hollow cylindrical body; and
    a distal face connected to a distal end of the elongate hollow distal portion.

5. The medical device connector shield of claim 4, wherein the elongate hollow distal portion is frustoconical in shape.

6. The medical device connector shield of claim 5, wherein the wire management port is defined in a sidewall of the frustoconical distal portion.

7. The medical device connector shield of claim 4, wherein the distal face of the portion cap portion is formed from a material with a greater thickness than a material that forms the elongate hollow distal portion.

8. The medical device connector shield of claim 1, wherein:
    the elongate hollow cylindrical body and the distal cap portion define a lumen;
    an electromechanical connector is disposed in the lumen; and
    a twisted pair of wires is electrically coupled with the electromechanical connector.

9. A medical device assembly, comprising:
    an elongate hollow cylindrical body that extends along a longitudinal axis;
    an elongate hollow distal portion that extends along the longitudinal axis, wherein a proximal end of the elongate hollow distal portion is connected to a distal end of the elongate hollow cylindrical body, wherein the elongate hollow distal portion is frustoconical in shape, and wherein the elongate hollow distal portion defines a wire management port extending through a sidewall of the elongate hollow distal portion; and a distal face connected to a distal end of the elongate hollow distal portion.

10. The medical device assembly of claim 9, further comprising a wire management tube that extends distally from the wire management port.

11. The medical device assembly of claim 10, wherein the wire management tube is formed from a flexible material and includes a service loop.

12. The medical device assembly of claim 11, further comprising an electromechanical connector disposed in a lumen defined by the elongate hollow cylindrical body, the elongate hollow distal portion, and the distal face, wherein a twisted pair of wires is connected to a distal end of the electromechanical connector, the twisted pair of wires extending distally through the wire management tube.

13. The medical device assembly of claim 9, further comprising a grommet disposed in the wire management port.

14. A medical device assembly, comprising:
 a connector shield formed from a magnetically permeable material, the connector shield including:
  an elongate hollow cylindrical body that extends along a longitudinal axis;
  an elongate hollow distal portion that extends along the longitudinal axis, wherein a proximal end of the elongate hollow distal portion is connected to a distal end of the elongate hollow cylindrical body, wherein the elongate hollow distal portion is frustoconical in shape, and wherein the elongate hollow distal portion defines a wire management port extending through a sidewall of the elongate hollow distal portion; and
  a distal face connected to a distal end of the elongate hollow distal portion, wherein the cylindrical body, distal portion, and distal face are formed from a magnetically permeable material; and
 an electromechanical connector disposed in a lumen defined by the connector shield, wherein a twisted pair of wires is connected to a distal end of the electromechanical connector, the twisted pair of wires extending distally through the wire management port.

15. The medical device assembly of claim 14, wherein the connector shield is disposed in a proximal end of a catheter actuator.

16. The medical device assembly of claim 14, wherein the wire management port is disposed off-axis with respect to the longitudinal axis.

17. The medical device assembly of claim 16, further comprising a wire management tube that extends distally from the wire management port, wherein the wire management tube forms a service loop, the twisted pair of wires extending through the wire management tube.

18. The medical device assembly of claim 17, wherein the service loop is helical in shape.

* * * * *